United States Patent [19]

Bergeron et al.

[11] Patent Number: 4,990,325

[45] Date of Patent: Feb. 5, 1991

[54] PROCESS FOR SYNTHESIS OF BERYLLIUM CHLORIDE DIETHERATE

[75] Inventors: Charles Bergeron, Baton Rouge, La.; John E. Bullard, Kendall Park, N.J.; Evan Morgan, Lynchburg, Va.

[73] Assignee: The Babcock & Wilcox Company, New Orleans, La.

[21] Appl. No.: 441,682

[22] Filed: Nov. 22, 1989

[51] Int. Cl.$^5$ ............................ C01B 3/02; C01B 7/00; C01F 3/00; C07C 43/12

[52] U.S. Cl. .............................. 423/648.1; 423/462; 423/476; 568/557

[58] Field of Search .................... 423/462, 496, 648.1; 568/557

[56] References Cited

U.S. PATENT DOCUMENTS

| | | | |
|---|---|---|---|
| 3,395,973 | 8/1968 | Winegartner et al. | 423/496 |
| 3,780,118 | 12/1973 | Carley et al. | 260/665 R |
| 3,812,213 | 5/1974 | Hall | 260/665 R |
| 3,822,320 | 7/1974 | Lamoria et al. | 568/557 |
| 3,830,906 | 8/1974 | Laran | 260/665 R |
| 3,865,928 | 2/1975 | Reigler et al. | 423/645 |
| 3,885,025 | 5/1975 | Lowrance | 423/645 |
| 3,917,809 | 11/1975 | Murib et al. | 423/645 |
| 3,919,320 | 11/1975 | Murib et al. | 564/463 |
| 3,991,121 | 11/1976 | Murib et al. | 568/557 |
| 4,581,065 | 4/1986 | Orgera | 75/84 |

OTHER PUBLICATIONS

Turova, N. Ya., Novoselva, A. V., and K. N. Semenenko, Solubility in the Beryllium Chloride Dietherate-Ethyl Ether System, Russian Journal of Inorganic Chemist, Jan. 1960, pp. 56–59.

Encyclopedia of Chemical Technology, Beryllium and Beryllium Alloys, Othmer, Kirk, latest edition.

Chemistry of Beryllium, Everest.

Beryllium, G. E. Darwin and J. H. Buddery.

Primary Examiner—Jeffrey E. Russel
Assistant Examiner—Brian M. Bolam
Attorney, Agent, or Firm—Vytas R. Matas; Robert J. Edwards; Daniel S. Kalka

[57] ABSTRACT

A low temperature method of producing beryllium chloride dietherate through the addition of hydrogen chloride gas to a mixture of beryllium metal in ether in a reaction vessel is described. A reflux condenser provides an exit for hydrogen produced form the reaction. A distillation condenser later replaces the reflux condenser for purifying the resultant product.

13 Claims, No Drawings

PROCESS FOR SYNTHESIS OF BERYLLIUM CHLORIDE DIETHERATE

The Government has rights in this invention pursuant to Contract No. BNL-307348-S awarded by the U.S. Department of Energy.

BACKGROUND OF THE INVENTION

1. Field of the Invention

The present invention relates in general to a method for producing beryllium chloride dietherate, and in particular, is directed to a low temperature method of producing beryllium chloride dietherate.

2. Description of the Related Art

Beryllium chloride is prepared by heating a mixture of beryllium oxide and carbon in chlorine at 600°–800° C. according to the following equation:

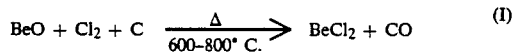
(I)

Alternative methods included the reaction of sulphur monochloride or phosgene with beryllium oxide, or the direct chlorination of beryllium carbide at 800° C.

Beryllium chloride is not conveniently made by direct hydrochlorination of beryllium oxide as is illustrated in the following reaction:

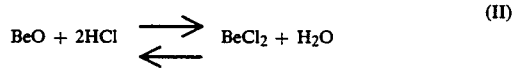
(II)

The equilibrium of the above reaction lies to the left except at very high temperatures.

A problem in the synthesis of beryllium chloride is the ease with which the tetrahydrate ($BeCl_2 \cdot 4H_2O$) undergoes hydrolysis during dehydration. Accordingly beryllium chloride is usually used under anhydrous conditions.

Numerous complexes of the type $BeCl_2X_2$, where X represents a wide variety of organic ligands, have been prepared either by direct interaction or by addition of the ligand to an ethereal solution of beryllium chloride. These types of complexes include pyridine, acetone, nitriles, aldehydes, quinoline, aliphatic amines, piperidine, thiourea, and tetrahydrofuran. All of these complexes are decomposed by water and must be prepared under anhydrous conditions.

One of the more important of the beryllium chloride addition complexes is the dietherate, $BeCl_2 \cdot 2Et_2O$. It is obtained by dissolving anhydrous beryllium chloride in dry ether which forms two liquid layers. The top layer is a solution of $BeCl_2 \cdot 2Et_2O$ in ether with the lower layer being a solution of ether in $BeCl_2 \cdot 2Et_2O$. The compound is crystallized from the lower layer.

Ether solutions of beryllium chloride are used as the starting material in the production of beryllium alkyls or other beryllium-organic compounds as taught in U.S. Pat. No. 3,262,888 for example. These solutions are generated by the addition of $BeCl_2$ to ether under anhydrous conditions. For example, U.S. Pat. No. 3,822,320 describes the synthesis of beryllium chloride monodiethyletherate.

Various approaches for the preparation of beryllium hydrides are disclosed in U.S. Pat. Nos. 3,865,928; 3,885,025; 3,917,809; 3,919,320; and 3,991,121.

Another reference of interest is U.S. Pat. No. 4,581,065 which discloses a process for metallothermic reduction of beryllium oxide, beryllium minerals and beryllium containing metal oxides.

A different approach in preparing beryllium chloride dietherate is described in U.S. Pat. No. 3,780,118 which discloses the use of a Soxhlet extractor. Beryllium metal chips are placed on top of a glass wool filter plug at one side and towards the top of the Soxhlet extractor. Reagent anhydrous diethyl ether is placed in the vessel below the Soxhlet extractor and hydrogen chloride is bubbled in through a wash bottle containing concentrated sulfuric acid. While this process is suitable for laboratory scale preparation of beryllium chloride dietherate, it does not offer a solution for the commercial manufacture of large quantities of beryllium compounds. Furthermore, the Soxhlet method requires the beryllium metal to be suspended away from the desired product. It is known in the art that there is difficulty in getting this reaction to proceed or go to completion when the beryllium metal is in contact with the beryllium chloride etherate.

Another problem in the production of beryllium chloride is the extremely high toxicity of beryllium particularly when it is in the form of easily volatile compounds such as beryllium chloride or beryllium fluoride ($BeF_2$).

Thus, there is a need for a low cost method for producing $BeCl_2 \cdot 2Et_2O$). The product must be capable of being purified in a simple and straightforward manner. Also, the process must produce $BeCl_2 \cdot 2Et_2O$ at a lower cost than the prior art methods by using low temperature equipment. There is also a need for this method to improve the health and safety conditions of the workers who may be exposed to the formation of toxic beryllium vapors at high temperatures.

SUMMARY OF THE INVENTION

The present invention solves the aforementioned problems in the prior art by providing a low temperature method of producing beryllium chloride dietherate.

The method comprises the steps of mixing beryllium metal with an ether directly in a reaction vessel. Hydrogen chloride gas is introduced into the reaction vessel below the surface of the ether. The hydrogen gas produced from the reaction is removed from the vessel. A reflux condenser attached to the reaction vessel facilitates the removal of the hydrogen gas. After the reaction is complete, the resulting mixture is distilled to purify the beryllium chloride ether solution.

One aspect of the present invention is to provide a low cost method which is commercially applicable.

Another aspect of the present invention is to produce ether solutions of beryllium chloride at a lower cost than the previously described methods with an improvement in the health and safety conditions of the workers by avoiding formation of beryllium vapors at high temperatures.

Still another aspect of the present invention is that the $BeCl_2 \cdot 2Et_2$ O produced is purified in a simple and straightforward manner by distilling the hydrogen chloride with the addition of ether to the distillation vessel.

The various features of novelty which characterize the invention are pointed out with particularity in the claims annexed to and forming part of this disclosure. For a better understanding of the present invention, and the operating advantages attained by its use, reference is made to the accompanying examples and descriptive matter in which a preferred embodiment of the invention is described.

DESCRIPTION OF THE PREFERRED EMBODIMENT

The present invention resides in a low temperature method of producing beryllium chloride etherate as contrasted with the high temperature methods of the prior art.

A beryllium chloride etherate solution is prepared by the addition of hydrogen chloride gas to a mixture of beryllium metal in an ether, such as diethyl ether for example. Other potentially suitable ethers include dialkyl ethers (diethyl ether, n-dipropylether, dibutylether, etc.), diaryl ethers (diphenyl ether, tolyl phenyl ether, ditolyl ether, etc.) and alkyl aryl ethers (anisole, ethyl phenyl ether, etc.)

The reaction occurs in a reaction vessel. While the illustrative examples employ a laboratory scale glass reaction vessel, suitable reaction vessels scaled for commercial operations are known to those skilled in this art. The reaction vessel is fitted with ports to allow for temperature measurement by a thermometer or other suitable temperature measuring means, a stirring shaft for a motor driven stirrer, a gas inlet tube which carries the hydrogen chloride gas below the surface of the ether, and a reflux condenser used to provide an exit port for the hydrogen gas evolved from the reaction. The reflux condenser is chilled with a refrigerated liquid such as freon for example to approximately at least $-4°$ C. or a temperature that returns as much of the ether to the reaction vessel as possible. The reaction that occurs is as follows:

$$2HCl + Be + 2Et_2O \rightarrow BeCl_2 \cdot 2Et_2O + H_2 \qquad (III)$$

It is known in the art how to produce metallic beryllium from ores. One process is based on the reduction of beryllium chloride by electrolysis in a bath of molten salts. Another process reduces beryllium fluoride with metallic magnesium. The present method employs beryllium metal which does not have to be pure, but must be the metal. Suitable grades of beryllium metal are supplied by Brush-Wellman including SP6565.

The resulting mixture of the beryllium chloride dietherate HCl and ether ($Et_2O$) is next distilled for purification purposes. The reflux condenser is removed from the reaction vessel and replaced with the distillation condenser. Heat is applied to the reaction vessel and the ether is distilled until the liquid in the reaction vessel reaches a temperature of about 50° C. This liquid is sampled and subsequently analyzed.

The present invention provides a low cost method which can be readily scaled for the commercial manufacture of large quantities of beryllium compounds. The $BeCl_2 \cdot 2Et_2O$ produced in accordance with the present invention is readily purified from an excess of the hydrogen chloride reactant in a simple and straightforward manner by distilling the hydrogen chloride while adding diethyl ether to the distillation vessel.

Moreover, this procedure improves the health and safety conditions of the workers by avoiding the formation of toxic beryllium vapors such as $BeCl_2$ or $BeF_2$ at high temperatures.

Understanding the present invention is further facilitated by referring to the subsequent examples, which indicate, without thereby limiting, ways in which the present invention is practiced.

EXAMPLE 1

A beryllium chloride solution was prepared by the addition of hydrogen chloride gas to a mixture of beryllium metal in diethyl ether. The reaction occurred in a glass reaction vessel fitted with ports to allow: (a) temperature measurement by a thermometer; (b) stirring shaft for a motor driven stirrer; (c) gas inlet tube which carried the HCl below the surface of the $Et_2O$ and (d) a reflux condenser used to provide an exit port for the hydrogen ($H_2$) produced by the reaction. The reflux condenser was chilled by refrigerated liquid to approximately $-4°$ C. to return as much of the $Et_2O$ to the reaction vessel as possible. The reaction that occurs can be written as;

$$2HCl + Be + 2Et_2O = BeCl_2 \cdot 2Et_2O + H_2$$

The resulting mixture of $BeCl_2$—$2Et_2O$, HCl and $Et_2O$ was subjected to distillation. The reflux condenser was removed from the reaction vessel and replaced with a distillation condenser. Heat was then applied to the reaction vessel and ether was distilled until the liquid in the reaction vessel reached a temperature of 50° C. This liquid was sampled and analyzed. The results of this analysis were:

| % Chloride | = | 28.68 |
|---|---|---|
| % Beryllium | = | 3.59 | with no detectable ethyl alcohol or ethyl chloride. The composition of this mixture can be calculated as:

| % $BeCl_2.2Et_2O$ | = | 90.83 |
|---|---|---|
| % HCl | = | 0.46 |
| % $Et_2O$ | = | 8.71 |

An ether solution of $BeCl_2$ has been generated which can be utilized as the required starting material for the production of beryllium-organic chemicals. This process does not require the use of high temperature furnaces nor the use of equipment not commonly found in the production of metallo-organic chemicals.

EXAMPLE 2

280 grams of ether was weighed into a flask fitted with a reflux condenser, thermometer, stirrer, and gas inlet. 6.3 grams of beryllium was added. The apparatus was assembled and the stirrer was started at 200 rpm. The temperature of the ether was 20° C. A cylinder of hydrogen chloride gas is fitted with a pressure regulator and rotameter. The flow of the hydrogen chloride into the flask was set to 222 ml/min. as read on the rotameter. After about 30 minutes, the temperature had risen to approximately 28° C. The hydrogen chloride was turned off after two hours and 21 minutes. Stirring was continued for another 49 minutes when no more beryllium was visible.

EXAMPLE 3

The same apparatus was used in this example as in the preceding one. 310 grams of ether was weighed into the flask and 6.74 grams of beryllium was added. The apparatus was assembled and the stirrer was started at 700 rpm. The hydrogen chloride flow was set to 222 ml/min. After about 36 minutes the temperature was approximately 30° C. and the stirrer was adjusted to 250 rpm. The hydrogen chloride was turned off after two hours and 36 minutes, and stirring was continued for another 30 minutes. The apparatus was changed to allow the excess ether to be distilled off.

| Reactants | |
| --- | --- |
| beryllium, moles | 0.748 |
| hydrogen chloride, moles | 1.496 |
| ether, milliliters | 434 |
| Product | |
| BeCl$_2$, moles | 0.748 |
| % Be | 3.59 |
| % Cl | 28.7 |
| ratio Cl/Be | 2.03/1.00 |
| ethanol | <0.001 |

While a specific embodiment of the invention has been shown and described in detail with examples to illustrate the application and the principles of the invention, certain modifications and improvements will occur to those skilled in the art upon reading the foregoing description. It is thus understood that all such modifications and improvements have been deleted herein for the sake of conciseness and readability but are properly in the scope of the following claims.

What is claimed is:

1. A low temperature method for producing beryllium chloride dietherate, comprising the steps of:
   mixing beryllium metal with an ether in a reaction vessel;
   introducing hydrogen chloride into the ether in the reaction vessel;
   removing hydrogen gas produced by the reaction with a reflux condenser; and
   distilling the resulting mixture to purify the beryllium chloride ether solution.

2. A method as defined in claim 1, wherein the step of introducing hydrogen chloride into the ether in the reaction vessel includes transporting hydrogen chloride gas below the surface of the ether.

3. A method as defined in claim 1, further comprising the step of chilling the reflux condenser to about −4° C.

4. A method as defined in claim 1, wherein the distilling step is carried out at a temperature of about 50° C.

5. A method as defined in claim 1, further comprising the step of agitating the reaction mixture for promoting the reaction.

6. A method as defined in claim 4, wherein the ether is diethyl ether.

7. A method as defined in claim 1, wherein the ether is a member selected from the group consisting of dialkyl ethers, diaryl ethers, and alkyl aryl ethers.

8. A low temperature method for producing beryllium chloride dietherate, comprising the steps of:
   mixing beryllium metal with an ether in a reaction vessel;
   introducing hydrogen chloride into the ether in the reaction vessel;
   removing hydrogen gas produced by the reaction by attaching a reflux condenser to the reaction vessel to provide an exit port for the hydrogen gas; and
   distilling the resulting mixture to purify the beryllium chloride ether solution.

9. A method as recited in claim 8, further comprising the step of chilling the reflux condenser to about −4° C.

10. A method as recited in claim 8, wherein the distilling step is carried out at a temperature of about 50° C.

11. A method as recited in claim 8, further comprising the step of agitating the reaction mixture for promoting the reaction.

12. A method as recited in claim 8, wherein the ether is diethyl ether.

13. A method as recited in claim 8, wherein the ether is a member selected from the group consisting of dialkyl ethers, diaryl ethers, and alkyl aryl ethers.

* * * * *